United States Patent
Case et al.

(10) Patent No.: US 7,361,189 B2
(45) Date of Patent: Apr. 22, 2008

(54) PROSTHETIC VALVE WITH PORES

(75) Inventors: Brian C. Case, Bloomington, IN (US); Beth Ann Kirts, Bloomington, IN (US); Thomas A. Osborne, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 124 days.

(21) Appl. No.: 11/216,504

(22) Filed: Aug. 31, 2005

(65) Prior Publication Data

US 2006/0058889 A1 Mar. 16, 2006

Related U.S. Application Data

(60) Provisional application No. 60/608,605, filed on Sep. 10, 2004.

(51) Int. Cl.
A61F 2/06 (2006.01)

(52) U.S. Cl. .................. 623/1.24; 623/23.68; 623/2.18

(58) Field of Classification Search ...... 623/1.24–1.26, 623/2.16–2.18, 2.36–2.37; 604/9
See application file for complete search history.

(56) References Cited

U.S. PATENT DOCUMENTS

| | | | |
|---|---|---|---|
| 4,328,592 A | 5/1982 | Klawitter | |
| 4,580,568 A | 4/1986 | Gianturco | |
| 5,628,791 A | 5/1997 | Bokros et al. | |
| 5,641,324 A | 6/1997 | Bokros et al. | |
| 5,908,452 A | 6/1999 | Bokros et al. | |
| 6,027,525 A | 2/2000 | Suh et al. | |
| 6,200,336 B1 | 3/2001 | Pavcnik et al. | |
| 6,231,598 B1 | 5/2001 | Berry et al. | |
| 6,287,334 B1 | 9/2001 | Moll et al. | |
| 6,299,635 B1 | 10/2001 | Frantzen | |
| 6,299,637 B1 * | 10/2001 | Shaolian et al. | 623/1.24 |
| 6,440,164 B1 * | 8/2002 | DiMatteo et al. | 623/1.24 |
| 6,464,720 B2 | 10/2002 | Boatman et al. | |
| 6,482,228 B1 | 11/2002 | Norred | |
| 6,494,909 B2 | 12/2002 | Greenhalgh | |
| 6,508,833 B2 | 1/2003 | Pavcnik et al. | |
| 6,676,698 B2 | 1/2004 | McGuckin, Jr. et al. | |
| 6,679,913 B2 * | 1/2004 | Homsy | 623/11.11 |
| 2001/0039450 A1 | 11/2001 | Pavcnik et al. | |
| 2002/0055772 A1 | 5/2002 | McGuckin, Jr. et al. | |
| 2002/0099439 A1 | 7/2002 | Schwartz et al. | |
| 2002/0177894 A1 | 11/2002 | Acosta et al. | |
| 2003/0083741 A1 | 5/2003 | Woo et al. | |
| 2003/0181974 A1 | 9/2003 | Xie et al. | |
| 2004/0093070 A1 | 5/2004 | Hojeibane et al. | |
| 2004/0117004 A1 | 6/2004 | Osborne et al. | |
| 2005/0137681 A1 | 6/2005 | Shoemaker et al. | |
| 2005/0137682 A1 * | 6/2005 | Justino | 623/1.24 |
| 2006/0282157 A1 | 12/2006 | Hill et al. | |

FOREIGN PATENT DOCUMENTS

| | | |
|---|---|---|
| EP | 1230901 A1 | 8/2002 |
| GB | 1598111 | 4/1977 |

* cited by examiner

*Primary Examiner*—Suzette Gherbi
(74) *Attorney, Agent, or Firm*—Dunlap, Codding & Rogers, P.C.; J. Matthew Buchanan (57) ABSTRACT

Prosthetic valves for regulating fluid flow are provided. The valves have at least one leaflet that includes a plurality of pores that allow a quantity of retrograde flow to pass through the leaflet when the valve is in a closed configuration.

16 Claims, 4 Drawing Sheets

PROSTHETIC VALVE WITH PORES

CROSS REFERENCE TO RELATED APPLICATION

This application claims priority to U.S. Provisional Application Ser. No. 60/608,605 filed on Sep. 10, 2004, the disclosure of which is hereby incorporated into this disclosure in its entirety.

FIELD OF THE INVENTION

The present invention relates to medical devices. More particularly, the invention relates to intraluminal valve prostheses.

BACKGROUND OF THE INVENTION

Many vessels in animal bodies transport fluids from one bodily location to another. Frequently, fluid flows in a unidirectional manner along the length of the vessel. Varying fluid pressures over time, however, can introduce a reverse flow direction in the vessel. In some vessels, such as mammalian veins, natural valves are positioned along the length of the vessel and act as one-way check valves that open to permit the flow of fluid in the desired direction and close to prevent fluid flow in a reverse direction, i.e., retrograde flow. The valves can change from an open position in response to a variety of circumstances, including changes in the cross-sectional shape of the vessel and the fluid pressure within the vessel.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of the valve leaflets to close. Furthermore, the leaflets may become damaged, such as by formation of thrombus and scar tissue, which may also affect the ability of the valve leaflets to close. Once valves are damaged, venous valve insufficiency may be present, which may lead to discomfort and possibly ulcers in the legs and ankles.

Current treatments for venous valve insufficiency include the use of compression stockings that are placed around the leg of a patient in an effort to force the vessel walls radially inward to restore valve function. Surgical techniques are also employed in which valves can be bypassed, eliminated, or replaced with autologous sections of veins having competent valves.

Minimally invasive techniques and instruments for placement of intraluminal medical devices have developed over recent years. A wide variety of treatment devices that utilize minimally invasive technology has been developed and includes stents, stent grafts, occlusion devices, infusion catheters and the like. Minimally invasive intravascular devices have especially become popular with the introduction of coronary stents to the U.S. market in the early 1990s. Coronary and peripheral stents have been proven to provide a superior means of maintaining vessel patency, and have become widely accepted in the medical community. Furthermore, the use of stents has been extended to treat aneurysms and to provide occlusion devices, among other uses.

Recently, prosthetic valves that are implantable by minimally invasive techniques have been developed. Frequently, a graft member is attached to a support frame and provides a valve function to the device. For example, the graft member can be in the form of a leaflet that is attached to a support frame and movable between first and second positions. In a first position, the valve is open and allows fluid flow to proceed through a vessel in a first direction, and in a second position the valve is closed to prevent fluid flow in a second, opposite direction. Examples of this type of prosthetic valve are described in commonly owned U.S. Pat. No. 6,508,833 to Pavcnik for a MULTIPLE-SIDED INTRALUMINAL MEDICAL DEVICE, U.S. Patent Application Publication No. 2001/0039450 to Pavcnik for an IMPLANTABLE VASCULAR DEVICE, and U.S. patent application Ser. No. 10/642,372, filed on Aug. 15, 2003, each of which is hereby incorporated by reference in its entirety. In other examples of prosthetic valves, a tube that terminates in leaflets is attached to one or more support frames to form a valve. The leaflets open to permit fluid flow in a first direction in response to fluid pressure on one side of the leaflets, and close to prevent fluid flow in a second, opposite direction in response to fluid pressure on opposite sides of the leaflets. An example of this configuration is provided in U.S. Pat. No. 6,494,909 to Greenhalgh for AN ENDOVASCULAR VALVE, which is hereby incorporated by reference in its entirety.

Natural valves can be somewhat 'leaky', allowing a relatively small quantity of fluid to flow in a reverse direction when the valve is in a closed position. It is believed that this leakiness is beneficial for several reasons. For example, it is believed that a small amount of retrograde flow limits the pooling of blood around the natural valve during periods of low pressure, which can reduce the formation of thrombus adjacent the valve leaflets and, therefore, increase the effective lifetime of the valve.

SUMMARY OF EXEMPLARY EMBODIMENTS OF THE INVENTION

The present invention provides valves for implantation in body vessels and other suitable environments. In one exemplary embodiment, a valve comprises a leaflet that has a valve portion that is moveable between first and second positions. In the first position, the leaflet permits fluid flow in a first direction through a body vessel in which the valve is implanted. In the second position, the leaflet substantially prevents fluid flow through the body vessel in a second, opposite direction. The leaflet defines a plurality of pores, and the valve includes a means for maintaining an axial position of the leaflet in the body vessel in which the valve is implanted.

In another exemplary embodiment, a valve comprises a support frame having radially compressed and radially expanded configurations. The valve includes at least one leaflet attached to the support frame that defines a plurality of pores. At least a portion of the at least one leaflet is moveable between first and second positions. In the first position, the leaflet permits fluid flow through a body vessel in which the valve is implanted. In the second position, the leaflet substantially prevents fluid flow through the body vessel, in a second, opposite direction.

The invention also provides methods of making valves. One exemplary method comprises a step of providing a support frame having radially compressed and radially expanded configurations, a step of providing at least one leaflet that defines a plurality of pores, and a step of attaching the at least one leaflet to the support frame. The leaflet is attached to the support frame so that at least a portion of the leaflet is moveable between first and second positions. In the first position, the leaflet permits fluid flow in a first direction through a body vessel in which the valve is implanted. In the second position, the leaflet substantially prevents fluid flow through the body vessel in a second, opposite direction.

Additional understanding of the invention can be obtained with review of the description of exemplary embodiments of the invention, appearing below, and the appended drawings that illustrate exemplary embodiments.

DETAILED DESCRIPTION OF EXEMPLARY EMBODIMENTS OF THE INVENTION

The following provides a detailed description of exemplary embodiments that reflect the invention. The description is not intended to limit the invention, or its protection, in any manner, but rather serves to enable those skilled in the art to make and use the invention.

The invention provides valves that can be used to regulate fluid flow through a body vessel. Accordingly, the valves of the invention can be implanted in a body vessel, or in any other suitable environment, to regulate the flow of fluid. Valves according to the invention can also be implanted in ducts, canals, and other passageways in the body, as well as cavities and other suitable locations. Valves according to exemplary embodiments of the invention can be implanted in the vessels of the vasculature, such as veins, to regulate the flow of blood through the vessels. The valves can be implanted in other suitable body vessels as well, such as arteries.

As used herein, the term "implanted," and grammatically related terms, refers to the positioning of an item in a particular environment, either temporarily, semi-permanently, or permanently. The term does not require a permanent fixation of an item in a particular position.

As used herein, the term "pore," and grammatically related terms, refers to a minute opening or orifice in a surface.

Figure 1:
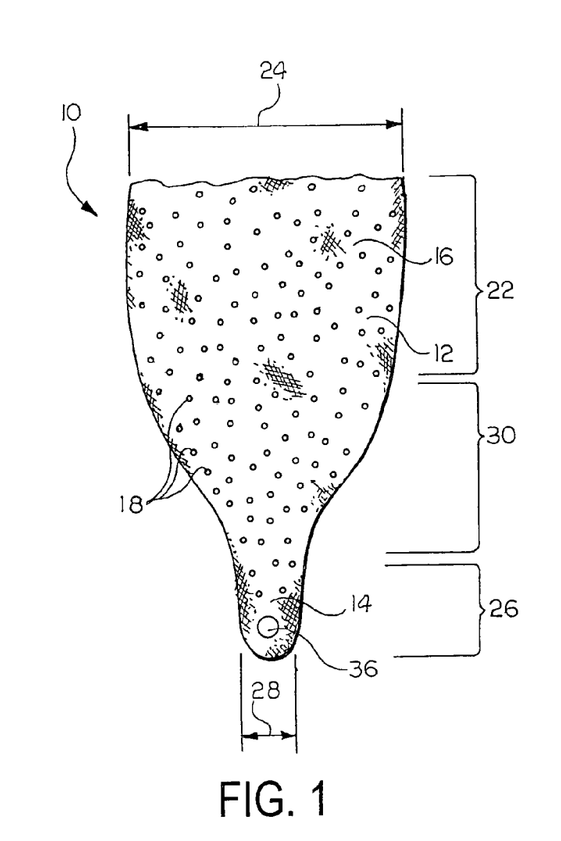
FIG. 1 is a perspective view of a valve according to a first exemplary embodiment of the invention.
Figure 2:
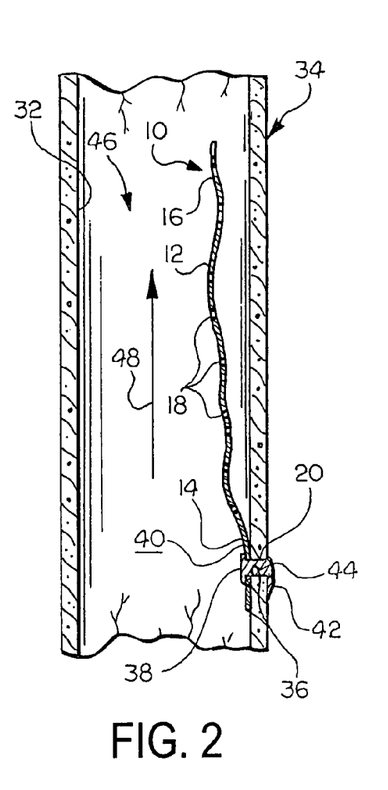
FIG. 2 is a sectional view of a body vessel containing the valve illustrated in FIG. 1. The valve is shown in an open configuration.
Figure 3:
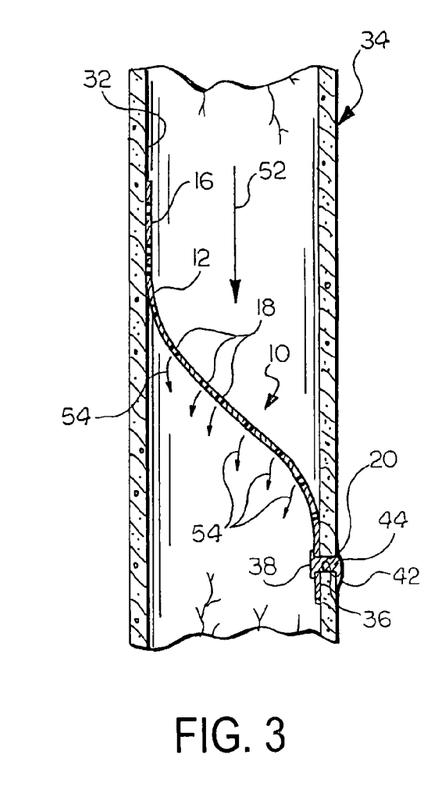
FIG. 3 is a sectional view of a body vessel containing the valve illustrated in FIG. 1. The valve is shown in a closed configuration.

FIGS. 1 through 3 illustrate a valve 10 according to a first exemplary embodiment. The valve 10 includes a leaflet 12 that has a base portion 14 and a valve portion 16. The leaflet 12 defines a plurality of pores 18. The valve 10 also includes a means for maintaining an axial position of the leaflet 12 in a body vessel in which the valve 10 is implanted.

Any suitable structure can be used as the means for maintaining an axial position of the leaflet 12 in a body vessel, and several exemplary structures are illustrated herein. The specific structure chosen for any particular valve will depend on several considerations, including the nature of the leaflet and the vessel in which the valve will be implanted. The structure need only be able to substantially maintain a position of the leaflet on an axis of a vessel in which the leaflet is implanted while fluid flows through the vessel. Examples of suitable structures for the means for maintaining an axial position include barbs, integrally formed anchors, support frames, and their equivalents. In the embodiment illustrated in FIGS. 1 through 3, the means for maintaining an axial position comprise a barb 20 that is structurally distinct from the leaflet 12.

The leaflet 12 comprises a section of material. The leaflet 12 can be formed of any suitable material, and need only be biocompatible or be able to be made biocompatible and be able to perform as described herein. The leaflet 12 advantageously can be formed of a flexible material. Examples of suitable materials for the leaflet 12 include natural materials, synthetic materials, and combinations of natural and synthetic materials. Examples of suitable natural materials include extracellular matrix (ECM) materials, such as small intestine submucosa (SIS), and other bioremodellable materials, such as bovine pericardium. Other examples of ECM materials that can be used in the valves of the invention include stomach submucosa, liver basement membrane, urinary bladder submucosa, tissue mucosa, and dura mater. Examples of suitable synthetic materials include polymeric materials, such as expanded polytetrafluoroethylene and polyurethane. ECM materials are particularly well-suited materials for use in the leaflet 12 at least because of their abilities to remodel and become incorporated into adjacent tissues. These materials can provide a scaffold onto which cellular in-growth can occur, eventually allowing the material to remodel into a structure of host cells. In one exemplary embodiment, the leaflet 12 is formed of an ECM material that has been stretched. The stretching is believed to increase the size of pores in the material. In another exemplary embodiment, SIS from a juvenile swine is used. The juvenile material is expected to be thinner than material from adult swine and thus more permissive of pore formation. Thoralon, a proprietary material available from Thoratec (Pleasanton, Calif.), is also a suitable material.

The leaflet 12 can have any suitable size and configuration, and the specific size and configuration chosen for the leaflet in a particular valve according to the invention will depend on several considerations, including the size, configuration, and/or nature of the vessel in which the valve will be implanted. In the embodiment illustrated in FIGS. 1 through 3, the leaflet 12 includes a first portion 22 having a first width 24, and a second portion 26 having a second width 28. The first width 24 is greater than the second width 28. Advantageously, the first portion 22 includes the valve portion 16. Also advantageously, the second portion 26 includes the base portion 14. In the illustrated embodiment, a transition region 30 is disposed between the first 22 and second 26 portions, and includes a width that tapers from the first width 24 to the second width 28.

As best illustrated in FIGS. 2 and 3, the base portion 14 provides a portion of the leaflet 12 that can be anchored to a wall 32 of a body vessel 34 in which the valve 10 is implanted. When the valve 10 is implanted in a body vessel, the base portion 14 remains substantially static, even as fluid flows through the body vessel 34, because the base portion 14 is associated with a means for maintaining an axial position of the leaflet 12 in the body vessel. For example, in the illustrated embodiment, the base portion 14 defines an opening 36. Barb 20 is partially disposed in the opening 36, with a head 38 disposed adjacent one surface 40 of the leaflet 12. An anchor portion 42 of the barb 20 is disposed external to the body vessel 34, and a body portion 44 of the barb 20 is disposed within the opening 36 and through the wall 32 of the body vessel 34. The head 38 and anchor portion 42 of the barb 20 can be compressed toward each other during implantation of the valve 10.

The barb 20 can be formed of any suitable material, and need only be biocompatible or able to be made biocompatible. Also, the barb 20 can have any suitable size and configuration, and the specific size and configuration chosen for any particular valve according to the invention will depend on several considerations, including the nature of the vessel in which the valve is being implanted. Also, the specific material used for the barb 20 can depend on the material used for the leaflet 12. For example, in embodiments in which the leaflet 12 comprises a bioremodellable material, such as SIS, the barb 20 can be formed of a resorbable material. As used herein, the term "resorbable" refers to the ability of a material to be absorbed into a tissue and/or body fluid upon contact with the tissue and/or body fluid. The contact can be prolonged, and can be intermittent in nature. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), and polyglycolide; trimethlyene carbonate; polycaprolactone; poly-beta hydroxy acids such as polyhydroxybutyrate and polyhydroxyvalerate; and other polymers such as polyphosphazines, polyorganophosphazines, polyanhydrides, polyesteramides, polyorthoesters, polyethylene oxide, polyester-ethers (e.g., polydioxanone) and polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

In embodiments in which the barb, or another suitable means for maintaining an axial position of the leaflet, comprises a resorbable material, the base portion 14 of the leaflet 12, or a portion thereof, can eventually become incorporated into the wall 32 of the body vessel 34, providing the desired anchoring function. Once the base portion 14 is sufficiently incorporated into the vessel wall 32, additional anchoring, such as that provided by the barb 20, may no longer be needed. If the barb 20 is formed of a resorbable material, the barb 20 would be elimintated gradually as the material of the barb 20 is absorbed, allowing the incorporated base portion 14 to perform the anchoring function.

As best illustrated in FIGS. 2 and 3, the valve portion 16 is moveable between first and second positions when the valve 10 is implanted in a body vessel 34. In the first position, illustrated in FIG. 2, the valve portion 16 is positioned within the body vessel 34 so that an opening 46 is formed between the vessel wall 32 and the valve portion 16. Fluid is able to flow through the body vessel 34 at the position of the valve 10 via the opening 46 in a first direction, represented by arrow 48. As such, the leaflet 12 can be referred to as being in an open configuration and as permitting fluid flow through the body vessel 34 in the first direction 48.

In the second position, illustrated in FIG. 3, a surface 50 of the valve portion 16 is disposed adjacent a portion of the wall 32 of the body vessel 34. In this configuration, the opening 46 of the first position, described above, is substantially eliminated. Accordingly, the leaflet 12 substantially prevents fluid flow through the body vessel 34 in a second, opposite direction, represented by arrow 52. As such, the leaflet 12 can be referred to as being in a closed configuration.

The valve portion 16 can move between the first and second positions, i.e., between open and closed configurations, in response to a change in the direction of fluid flow through a body vessel in which the valve 10 is implanted, such as a change from flow in the first direction 48 to a flow in the second, opposite direction 52. Also, the valve portion 16 can move between the first and second positions in response to a change in fluid pressure on one or more sides of the leaflet 12.

As best illustrated in FIG. 3, the pores 18 allow an amount of fluid to flow through the leaflet 12 in the second, opposite direction 52. That is, the pores 18 allow a quantity of retrograde flow to pass through the leaflet 12 when the leaflet 12 is in the closed configuration. This retrograde flow is represented by arrows 54 in FIG. 3.

The pores 18 can have any suitable size and configuration, and the specific size and configuration chosen will depend on several considerations, such as the desired quantity and/or rate of retrograde flow for a particular valve. In exemplary embodiments, the total open area provided by all pores 18 is advantageously sized to mimic the degree of retrograde flow—the leakiness—of a natural valve that is typically present at or near a particular point of treatment. For venous valve applications, the total open area of the pores 18 is advantageously less than about 50% of the cross-sectional area of the vessel at the intended point of implantation. More advantageously, the total open area of the pores 18 is less than about 25% of the total cross-sectional area of the vessel at the intended point of implantation. In one example, a device is configured for placement in a vessel having a total cross-sectional area of about 50 $mm^2$. In this example, the pores 18 have a total open area of about 20 $mm^2$. Also for venous valve applications, circular pores have been found to be suitable but it is noted that any suitable shape can be used. Individual pores can have any suitable size, but should be large enough to allow fluid of a type typically found in the vessel type in which the valve 10 will be implanted to pass through the pore. For valves intended for use in blood vessels, a pore can be large enough to allow both fluid and cellular components of blood to pass through the pore. Alternatively, the pore can be sized to allow the fluid component of blood to pass through the pore while substantially preventing the cellular components of blood to pass through the pore. This sizing of the pore may advantageously produce a cellular deposit on a surface of the leaflet while allowing the desired retrograde flow. It is noted that the pores illustrated in all drawings are not necessarily drawn to scale, either absolutely or relative to other components of the illustrated valve or vessel.

Currently contemplated pore sizes for venous valve applications include pore diameters of between about 0.1 μm and about 10 mm, pore diameters of between about 0.1 μm and about 1 mm, pore diameters of between about 0.1 μm and about 0.1 mm, and pore diameters of between about 0.1 μm and about 1 μm. These pore sizes are expected to provide the desired retrograde flow in a venous environment while not eliminating the ability of the leaflet to regulate antegrade flow. The specific pore size chosen for any particular valve according to the invention will depend on several considerations, including the type of fluid that typically flows through the body vessel in which the valve will be implanted.

In the embodiment illustrated in FIGS. 1 through 3, the pores 18 are substantially uniform in size and configuration and are positioned on both the valve 16 and base 14 portions of the leaflet 12.

The pores 18 can be formed in any suitable manner, including by punching or stamping the leaflet 16 with a suitable die. Also, the pores can be formed in some materials using a laser to form the openings of the pores. Chemical processes, such as salt extraction techniques, can be used to form pores in the leaflet 16. It is understood that all pore-forming techniques can be conducted directly on the leaflet 16 or on a material used to form the leaflet 16. For example, a sheet of material can be treated to create pores and the sheet can subsequently be divided into sections that can be used as leaflets. It is also understood that the pores 18 can comprise pores naturally present in a material used to form the leaflet 16, such as a porous membrane.

Figure 4:
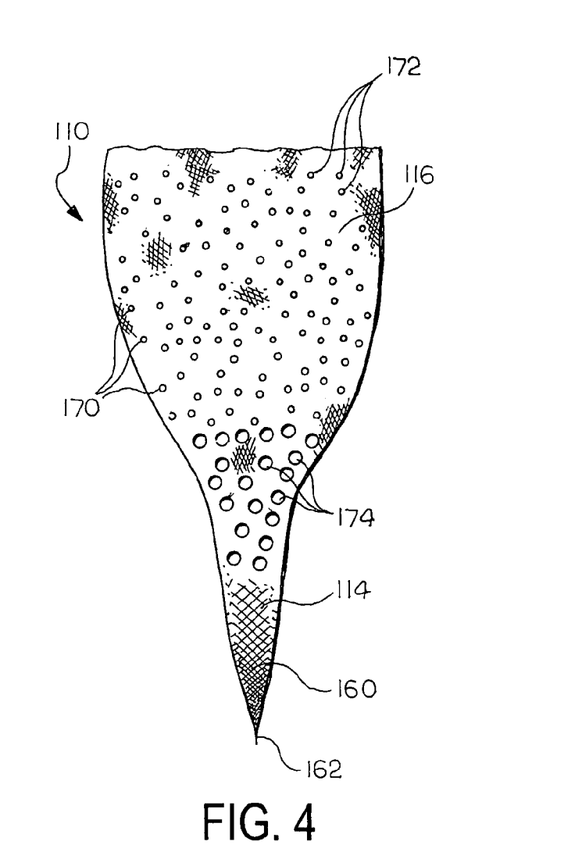
FIG. 4 is a perspective view of a valve according to a second exemplary embodiment of the invention.
Figure 5:
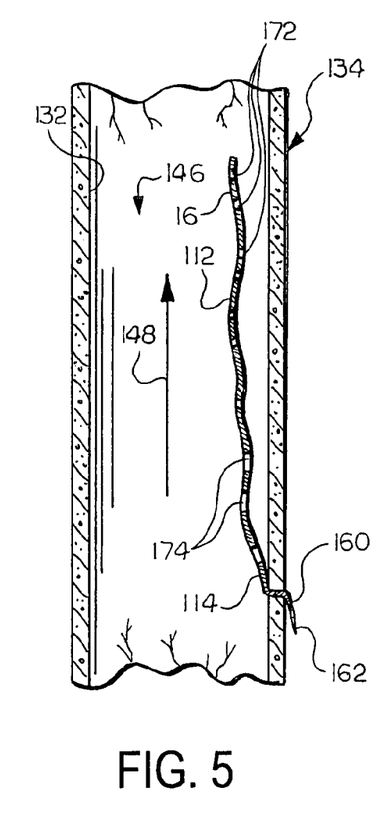
FIG. 5 is a sectional view of a body vessel containing the valve illustrated in FIG. 4. The valve is shown in an open configuration.
Figure 6:
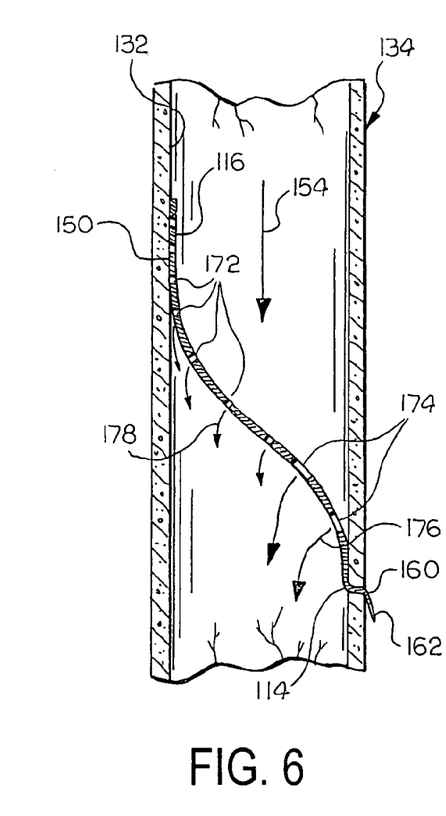
FIG. 6 is a sectional view of a body vessel containing the valve illustrated in FIG. 4. The valve is shown in a closed configuration.

FIGS. 4 through 6 illustrate a valve 110 according to a second exemplary embodiment of the invention. The valve 110 according to this embodiment is similar to the embodiment illustrated in FIGS. 1 through 3, except as described below. Accordingly, the valve 110 includes a leaflet 112 that has base 114 and valve 116 portions. The valve 110 includes a means for maintaining an axial position of the leaflet 112 in a body vessel in which the valve 110 is implanted. In the embodiment illustrated in FIGS. 4 through 6, the means for maintaining an axial position comprise an anchor portion 160 integrally formed by the leaflet 112.

The anchor portion 160 is integrally formed by the leaflet and is relatively more rigid than another portion of the leaflet, such as the valve portion 116. The anchor portion 160 is advantageously sufficiently rigid for passage through a wall 132 of a body vessel 134 in which the valve 110 is implanted upon application of a suitable force. The anchor portion 160 of the leaflet 112 in the embodiment illustrated in FIG. 4 defines a point 162 that facilitates an initial passage into a vessel wall 132 during implantation.

The anchor portion 160 can be formed in any suitable manner for creating the desired relative rigidity. The specific technique chosen for forming anchoring portion 160 will depend on several considerations, including the nature of the material used for the leaflet 112. In embodiments in which the leaflet 112 is formed of an ECM material, the anchor portion 160 can be formed by chemically fixing that portion of the leaflet 112 or by attaching additional layers of material to that portion of the leaflet 112.

In this embodiment, the leaflet 112 defines a plurality of pores 170 that includes first 172 and second 174 sets of pores. The first set 172 of pores has a first mean diameter, and the second set 174 has a second mean diameter. The second mean diameter is greater than the first mean diameter. Each set of pores 172, 174 can include individual pores having any suitable size, as described above, and the pores in a set 172, 174 do not necessarily have to be uniform in size. As best illustrated in FIG. 6, pores of the second set 172 of pores are able to allow a greater quantity of retrograde flow, represented by arrows 176, to pass through the leaflet 112 than the quantity allowed to pass by pores of the first set 172, represented by arrows 178. Pores of each set 172,174 can have any suitable size that provides the desired difference in mean diameters. In one exemplary embodiment, pores of the first set 172 are sized to allow passage of only the fluid component of blood, and pores of the second set 174 are sized to allow passage of both the fluid and cellular components of blood.

The second set 174 of pores can be positioned on any desired portion of the leaflet 112. Advantageously, the second set 174 of pores is positioned on and/or near the base portion 114 of the leaflet 112, with the first set 172 positioned on the valve portion 116 of the leaflet 112. This positioning is expected to facilitate flushing of a pocket 180 formed between the leaflet 112 and the vessel wall 132 when the leaflet 112 is in the closed configuration.

The valve 110 according to this embodiment is implanted in a body vessel 134 by passing a portion of the anchor portion 160 through a wall 132 of the vessel 134. Once the valve 110 is implanted, the base portion 114 remains substantially static, while the valve portion 116 moves between a first position, illustrated in FIG. 5, and a second position, illustrated in FIG. 6. In the first position, an opening 146 is formed between the vessel wall 132 and the leaflet 112. Fluid is able to flow through the body vessel 134 at the position of the valve 110 via the opening 146 in a first direction, represented by arrow 148. In the second position, a surface 150 of the valve portion 116 is disposed adjacent a portion of the wall 132 of the body vessel 134. In this configuration, the opening 146 is substantially eliminated. Accordingly, the leaflet 112 substantially prevents fluid flow through the body vessel 134 in a second, opposite direction, represented by arrow 154. As described above, though, the first 172 and second 174 sets of pores allow quantities of retrograde flow, represented by arrows 178, 176 respectively, to flow through the body vessel 134.

Figure 7:
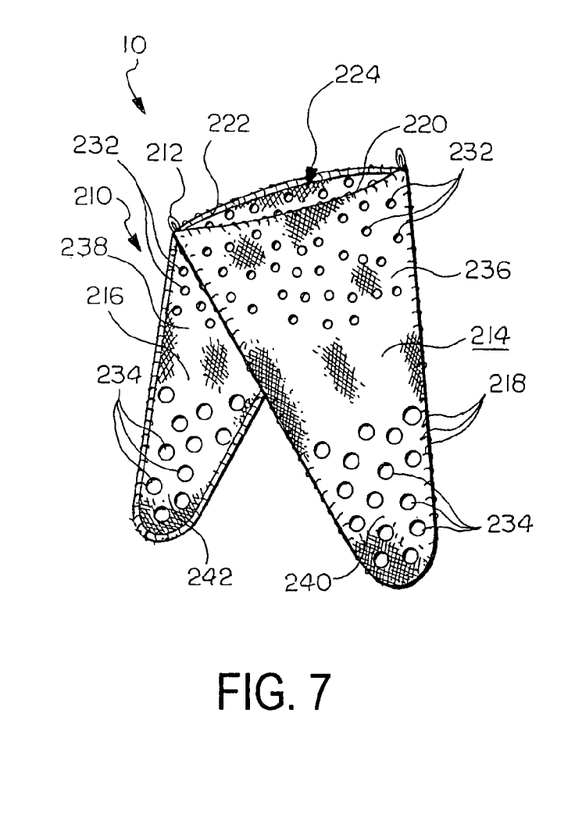
FIG. 7 is a perspective view of a valve according to a third exemplary embodiment of the invention.
Figure 8:
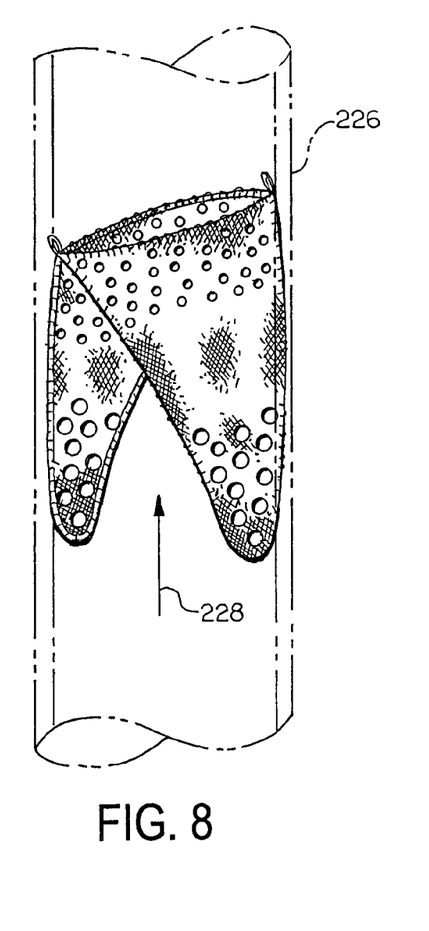
FIG. 8 is a perspective view of the valve illustrated in FIG. 7 disposed within a body vessel. The valve is shown in an open configuration.
Figure 9:
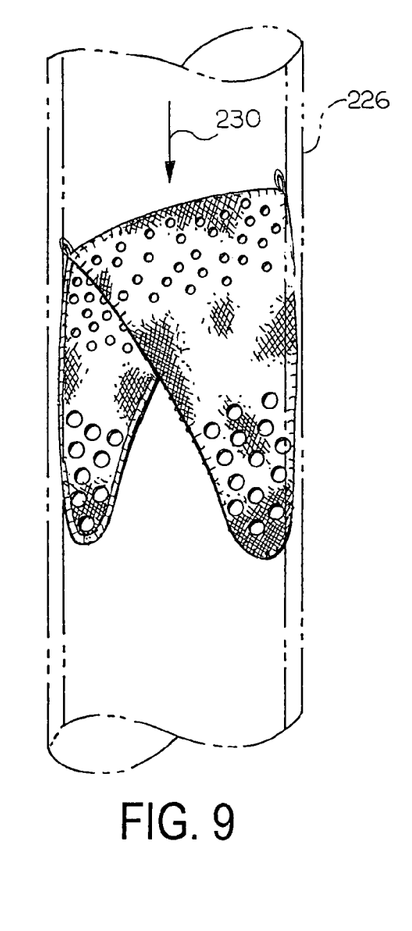
FIG. 9 is a perspective view of the valve illustrated in FIG. 7 disposed within a body vessel. The valve is shown in a closed configuration.

FIGS. 7 through 9 illustrate a valve 210 according to a third exemplary embodiment of the invention. The valve 210 of this embodiment includes a support frame 212 and first 214 and second 216 leaflets attached to the support frame 212. The leaflets 214, 216 are attached to the support frame 212 with a suitable attachment element, such as sutures 218.

If an optional support frame is included in any particular valve, any suitable support frame can be used. The specific support frame chosen will depend on several considerations, including the size and configuration of the vessel and the size and nature of the leaflet.

The support frame chosen need only provide a structure for attachment of the leaflets 214, 216. A support frame that provides a stenting function, i.e., exerts a radially outward force on the interior of the vessel in which the valve 210 is implanted, can be utilized if desired. By including a support frame that provides a stenting function, the valve 210 can provide both stenting and valving functionality at a point of treatment. The stent art provides numerous examples of support frames acceptable for use in the valve 210, and any suitable stent support frame can be used. The specific stent support frame chosen will depend on several factors, including the vessel in which the medical device is being implanted, the axial length of the treatment site, the number of valves desired in the device, the inner diameter of the vessel, the delivery method for placing the support structure, and others. Those skilled in the art can determine an appropriate support structure based on these and other factors.

The support frame 212 is an expandable support frame having radially compressed and radially expanded configurations. The support frame 212 can be either balloon—or self—expandable. Also, the support frame can be formed from a variety of materials, and need only be biocompatible, or able to be made biocompatible, and provide for the attachment of the leaflets 214, 216 and stenting function, if desired. Examples of suitable materials include, without limitation, stainless steel, nickel titanium (NiTi) alloys, e.g., Nitinol, other shape memory and/or superelastic materials, polymers, and composite materials. A resorbable material can also be used for the support frame 212. A number of resorbable materials are known in the art, and any suitable resorbable material can be used. Examples of suitable types of resorbable materials include resorbable homopolymers, copolymers, and blends of resorbable polymers. Specific examples of suitable resorbable materials include poly-alpha hydroxy acids such as polylactic acid, polylactide, polyglycolic acid (PGA), and polyglycolide; trimethlyene carbonate; polycaprolactone; poly-beta hydroxy acids such as polyhydroxybutyrate or polyhydroxyvalerate; and other polymers such as polyphosphazines, polyorganophosphazines, polyanhydrides, polyesteramides, polyorthoesters, polyethylene oxide, polyester-ethers (e.g., polydioxanone) and polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

Suitable support frames can also have a variety of configurations, including braided strands, helically wound strands, ring members, consecutively attached ring members, tube members, and frames cut from solid tubes. Also, suitable support frames can have a variety of sizes. The exact configuration and size chosen will depend on several factors, including the desired delivery technique, the nature of the vessel in which the device will be implanted, and the size of the vessel. The support frame can be sized so that the second, expanded configuration is larger in diameter that the inner diameter of the vessel in which the device will be implanted. This sizing can facilitate maintenance of the device in the vessel following implantation.

Examples of suitable support frames for use in the medical devices of the invention include those described in U.S. Pat. No. 6,508,833 to Pavcnik et al. for a MULTIPLE-SIDED INTRALUMINA MEDICAL DEVICE; U.S. Pat. No. 6,464,720 to Boatman et al. for a RADIALLY EXPANDABLE STENT; U.S. Pat. No. 6,231,598 to Berry et al. for a RADIALLY EXPANDABLE STENT; U.S. Pat. No. 6,299,635 to Frantzen for a RADIALLY EXPANDABLE NON-AXIALLY CONTRACTING SURGICAL STENT; U.S. Pat. No. 4,580,568 to Gianturco for a PERCUTANEOUS ENDOVASCULAR STENT AND METHOD FOR INSERTION THEREOF; and published application for U.S. Patent 20010039450 to Pavcnik et al. for an IMPLANTABLE MEDICAL DEVICE, all of which are hereby incorporated by reference in their entirety for the purpose of describing suitable support frames.

The support frame 212 can include structural features, such as barbs, that maintain the support frame 212 in position following implantation in a body vessel. The art provides a wide variety of structural features that are acceptable for use in the support frame 212, and any suitable structural feature can be used. Furthermore, barbs can also comprise separate members attached to the support frame 212 by suitable attachment means and techniques, such as welding and bonding.

The first leaflet 214 has an edge 220 that is free of the support frame 212. Similarly, the second leaflet has an edge 222 that is free of the support frame. The edges 220, 222 cooperatively define a valve opening 224. When the valve 210 is in an open configuration, illustrated in FIG. 8, the opening 224 is present and allows fluid to flow through a body vessel 226 in a first direction, represented by arrow 228. When the valve 210 is in a closed configuration, illustrated in FIG. 9, the edges 220, 222 are adjacent each other and the opening (not referenced in FIG. 9) is substantially eliminated. In this configuration the valve 210 substantially prevents fluid from flowing through the vessel 226 in a second, opposite direction, represented by arrow 230.

Each leaflet 214, 216 includes first 232 and second 234 sets of pores. Similar to the embodiment illustrated in FIGS. 4 through 6, the first set 232 is positioned on valve portions 236, 238 of the first 214 and second 216 leaflets, while the second set 234 is positioned on and/or adjacent base portions 240, 242 of the first 214 and second 216 leaflets. This positioning is expected to be advantageous for the same reasons described above for the embodiment illustrated in FIGS. 4 through 6.

In this embodiment, the leaflets 214, 216 include intermediate regions 244, 246 that is substantially free of pores. The intermediate region can have any suitable size and configuration. In exemplary embodiments, the intermediate region has an axial length that is equal to or greater than an axial length of a region of a leaflet on which one of the first 232 and second 234 sets of pores is positioned.

Figure 10:
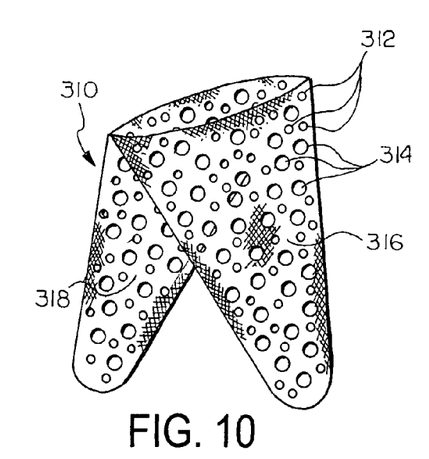
FIG. 10 is a perspective view of a valve according to a fourth exemplary embodiment of the invention.

FIG. 10 illustrates a valve 310 according to a fourth exemplary embodiment of the invention. The valve 310 according to this embodiment is similar to the valve illustrated in FIGS. 7 through 9 and described above. However, in this embodiment, first 312 and second 314 sets of pores are interspersed with each other on first 316 and second 318 leaflets. Thus, each set 312, 314 of pores is not restricted to any particular portion or region of the leaflets 316, 318. Also, similar to the embodiments described above, the second set 314 has a mean diameter that is greater than a mean diameter of the first set 312 of pores. Further, in this embodiment, both sets 312, 314 of pores are disposed at varying intervals over the entire surface of the leaflets 316, 318.

In embodiments in which two sets of pores are present, such as the embodiments illustrated in FIGS. 4, 7, and 10, it is understood that the pores of the two sets can be segregated from each other or interspersed with each other. Also, each set of pores can be disposed on any given section of a leaflet, irrespective of pore size. It is also understood that the pores of two sets of pores can differ in a characteristic other than size. For example, two sets of pores can be used in which both sets have the same mean diameter but the pores of one set are defined by an edge, e.g., a scalloped edge, that is different than an edge, e.g., a smooth edge, that defines the pores of the second set.

Figure 11:
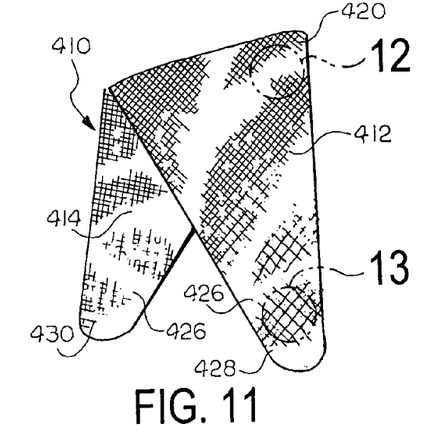
FIG. 11 is a perspective view of a valve according to a fifth exemplary embodiment of the invention.
Figure 12:
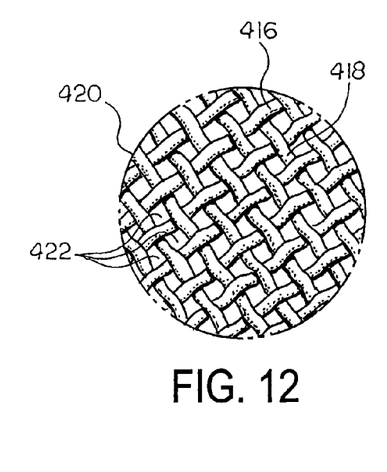
FIG. 12 is a magnified view of the area referenced in FIG. 11.
Figure 13:
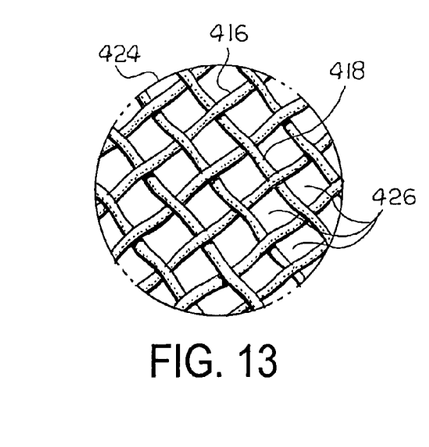
FIG. 13 is a magnified view of the area referenced in FIG. 11.

FIGS. 11 through 13 illustrate a valve 410 according to a fifth exemplary embodiment of the invention. In this embodiment, the leaflets 412, 414 each comprise a mesh of interwoven fibers 416, 418. FIGS. 12 and 13 illustrate magnified views of the mesh of the leaflets 412.

The fibers 416, 418 are interwoven to form pores. The fibers 416, 418 can be woven together in a regular pattern to produce pores of consistent size, or can be woven at random or varying angles to produce pores of differing sizes. In the embodiment illustrated in FIGS. 11 through 13, each leaflet 412, 414 includes a first portion 420, shown magnified in FIG. 12, that includes pores 422 having a first mean open area. Also, each leaflet 412, 414 includes a second portion 424, shown magnified in FIG. 13, that includes pores 426 having a second mean area. The second mean area is greater than the first mean area.

The first 422 and second 426 pores can be positioned in any desired relative positions on one or both leaflets 412, 414. It is expected that a positioning that places the pores 426 having the second, larger mean area at and/or adjacent base portions 428, 430 of the leaflets 412, 414 is advantageous for the same reasons as described above for other embodiments.

The fibers 416, 418 can be any suitable fiber, including fibers of polymeric materials. Also, the leaflets 412, 414 of this embodiment can be formed using any suitable technique for forming a mesh out of fibers, including weaving and electrostatic spinning.

Figure 14:
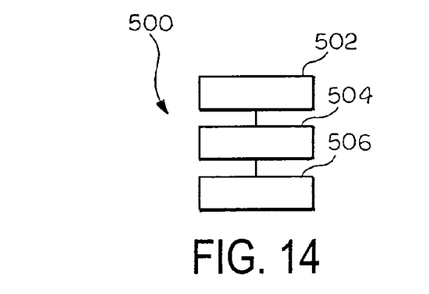
FIG. 14 is a block diagram illustrating a method of making a valve according to the invention.

The invention also provides methods of making valves. FIG. 14 is a block diagram illustrating an exemplary method 500 according to the invention. The method 500 includes the step 502 of providing a support frame having radially compressed and radially expanded configurations. Another step 504 comprises providing at least one leaflet that defines a plurality of pores. Another step 506 comprises attaching the at least one leaflet to the support frame so that at least a portion of the leaflet is moveable between first and second positions. In the first position, the leaflet permits fluid flow in a first direction through a body vessel in which the valve is implanted. In the second position, the leaflet substantially prevents fluid flow through the body vessel in a second, opposite direction. The pores allow a quantity of retrograde flow to pass through the leaflet in the second, opposite direction when the leaflet is in the second position.

Valves according to the invention can be implanted at a particular point of treatment using any suitable technique, including surgical placement and delivery by minimally invasive procedures using suitable delivery devices.

The foregoing detailed description provides exemplary embodiments of the invention and includes the best mode for practicing the invention. These embodiments are intended only to serve as examples of devices that reflect the invention and not to limit the scope of the invention, or its protection, in any manner.

We claim:

1. A valve for regulating fluid flow through a body vessel, the valve comprising:
   a leaflet having a valve portion moveable between a first position that permits said fluid flow in a first direction and a second position that substantially prevents said fluid flow in a second, opposite direction, the leaflet defining a plurality of pores, the valve portion having a first portion and a second portion, a first pore of the plurality of pores is disposed on the first portion, and a second pore of the plurality of pores is disposed on the second portion, wherein the first pore has a first diameter and the second pore has a second, different diameter; and
   means for maintaining an axial position of the leaflet in said body vessel.

2. A valve for regulating fluid flow through a body vessel according to claim 1 wherein at least one pore of the plurality of pores has a diameter between about 0.1 µm and about 10 mm.

3. A valve for regulating fluid flow through a body vessel according to claim 1, wherein at least one pore of the plurality of pores has a diameter between about 0.1 µm and about 1 mm.

4. A valve for regulating fluid flow through a body vessel according to claim 1, wherein at least one pore of the plurality of pores has a diameter between about 0.1 µm and about 0.1 mm.

5. A valve for regulating fluid flow through a body vessel according to claim 1, wherein at least one pore of the plurality of pores has a diameter between about 0.1 µm and about 1 µm.

6. A valve for regulating fluid flow through a body vessel according to claim 1, wherein the plurality of pores has a mean diameter of between about 0.1 µm and about 10 mm.

7. A valve for regulating fluid flow through a body vessel according to claim 1, wherein the plurality of pores has a mean diameter of between about 0.1 µm and about 1 mm.

8. A valve for regulating fluid flow through a body vessel according to claim 1, wherein the plurality of pores has a mean diameter of between about 0.1 µm and about 0.1 mm.

9. A valve for regulating fluid flow through a body vessel according to claim 1, wherein the plurality of pores has a mean diameter of between about 0.1 µm and about 1 µm.

10. A valve for regulating fluid flow through a body vessel according to claim 1, wherein the second diameter is larger than the first diameter.

11. A valve for regulating fluid flow through a body vessel according to claim 1, wherein the leaflet is formed of a bioremodellable material.

12. A valve for regulating fluid flow through a body vessel according to claim 11, wherein the bioremodellable material comprises an extracellular matrix material.

13. A valve for regulating fluid flow through a body vessel, the valve comprising:
   a leaflet having a valve portion moveable between a first position that permits said fluid flow in a first direction and a second position that substantially prevents said fluid flow in a second, opposite direction, the leaflet comprising bioremodellable material and defining a plurality of pores, wherein the bioremodellable material comprises small intestine submucosa; and,
   means for maintaining an axial position of the leaflet in said body vessel.

14. A valve for regulating fluid flow through a body vessel according to claim 1, wherein the leaflet comprises a mesh.

15. A valve for regulating fluid flow through a body vessel, the valve comprising:
   a support frame having radially compressed and radially expanded configurations; and
   at least one leaflet attached to the support frame and defining a plurality of pores, at least a portion of the leaflet being movable between a first position that permits fluid flow through said body vessel and a second position that substantially prevents fluid flow through said body vessel, wherein the plurality of pores comprises first and second sets of pores, the first set of pores having a first mean diameter and the second set of pores having a second mean diameter that is different than the first mean diameter.

16. A valve for regulating fluid flow through a body vessel according to claim 15, wherein the leaflet comprises first and second regions and the first set of pores is disposed on the first region and the second set of pores is disposed on the second region.

* * * * *